United States Patent [19]

Marker

[11] Patent Number: 5,614,065
[45] Date of Patent: *Mar. 25, 1997

[54] DISTILLATION WITH MEMBRANE APPARATUS

[75] Inventor: Terry L. Marker, Warrenville, Ill.

[73] Assignee: UOP, Des Plaines, Ill.

[*] Notice: The term of this patent shall not extend beyond the expiration date of Pat. No. 5,565,066.

[21] Appl. No.: 328,794

[22] Filed: Oct. 31, 1994

[51] Int. Cl.$^6$ .................... B01D 3/14; B01J 8/04
[52] U.S. Cl. ............... 202/158; 202/162; 202/172; 202/182; 202/267.1; 422/191; 422/193; 422/211; 422/213; 210/500.23; 210/640
[58] Field of Search ............... 422/191, 193, 422/211, 213; 159/DIG. 28; 202/158, 162, 172, 267.1, 182; 203/18, 29, 41, 75, 78, 80, DIG. 6; 96/10; 95/50; 210/640, 500.23

[56] References Cited

U.S. PATENT DOCUMENTS

| | | | |
|---|---|---|---|
| 3,122,486 | 2/1964 | Skarstrom | 202/42 |
| 3,844,898 | 10/1974 | De Graff | 202/158 |
| 4,345,973 | 8/1982 | Ladisch et al. | 203/19 |
| 4,407,662 | 10/1983 | Girder | 203/19 |
| 4,478,685 | 10/1984 | Mortenson | 262/158 |
| 4,617,093 | 10/1986 | Hwang | 202/158 |
| 4,774,365 | 9/1988 | Chen et al. | 568/697 |
| 4,802,987 | 2/1989 | Black | 210/640 |
| 4,820,418 | 4/1989 | Hirotsu et al. | 210/640 |
| 4,874,524 | 10/1989 | Liapis et al. | 203/41 |
| 4,895,989 | 1/1990 | Sunder et al. | 568/851 |
| 4,906,787 | 3/1990 | Huang et al. | 568/697 |
| 4,913,818 | 4/1990 | Van Wijk et al. | 210/500.27 |
| 4,915,834 | 4/1990 | Bruschke | 210/321.84 |
| 4,978,430 | 12/1990 | Nakagawa et al. | 203/14 |
| 5,059,327 | 10/1991 | Takegami | 210/500.34 |
| 5,066,403 | 10/1991 | Dutta et al. | 210/638 |
| 5,085,778 | 2/1992 | Reale, Jr. | 210/500.39 |
| 5,156,740 | 10/1992 | Bruschke | 210/490 |
| 5,160,046 | 11/1992 | Pasternak | 210/640 |
| 5,232,085 | 8/1993 | Hayashi et al. | 202/182 |
| 5,235,102 | 8/1993 | Palmer et al. | 562/607 |
| 5,282,968 | 2/1994 | Lee | 210/640 |
| 5,300,197 | 4/1994 | Mitani et al. | 202/177 |
| 5,324,866 | 6/1994 | Marker et al. | 568/697 |
| 5,395,981 | 3/1995 | Marker | 568/697 |
| 5,449,501 | 9/1995 | Luebke et al. | 422/193 |

FOREIGN PATENT DOCUMENTS

| | | | |
|---|---|---|---|
| 561125 | 7/1958 | Canada . | |
| 4551125 | 7/1958 | Canada | 203/41 |

OTHER PUBLICATIONS

Ming Z; Chan–Jian, X; Guo-Cong, Y, Progess in Natural Science Jun. 1994, vol. 14, No. 5.

*Primary Examiner*—Nina Bhat
*Attorney, Agent, or Firm*—Thomas K. McBride; Eugene I. Snyder; Maryann Maas

[57] ABSTRACT

An apparatus for separating a first component of a process stream from a second component of a process stream in a single vessel has been developed. The single vessel apparatus has a membrane contactor dividing the vessel into an upper portion and a lower portion where the membrane contactor is a material providing selective permeation of fluid components and restricting passage of at least one component to the upper portion of the vessel, and a plurality of vertically spaced apart distillation contactors disposed within the vessel for vapor and liquid distillation located in the lower and/or upper portion of the vessel. The benefit is the production of a process stream that is of high first component purity at reduced capital equipment costs.

19 Claims, 1 Drawing Sheet

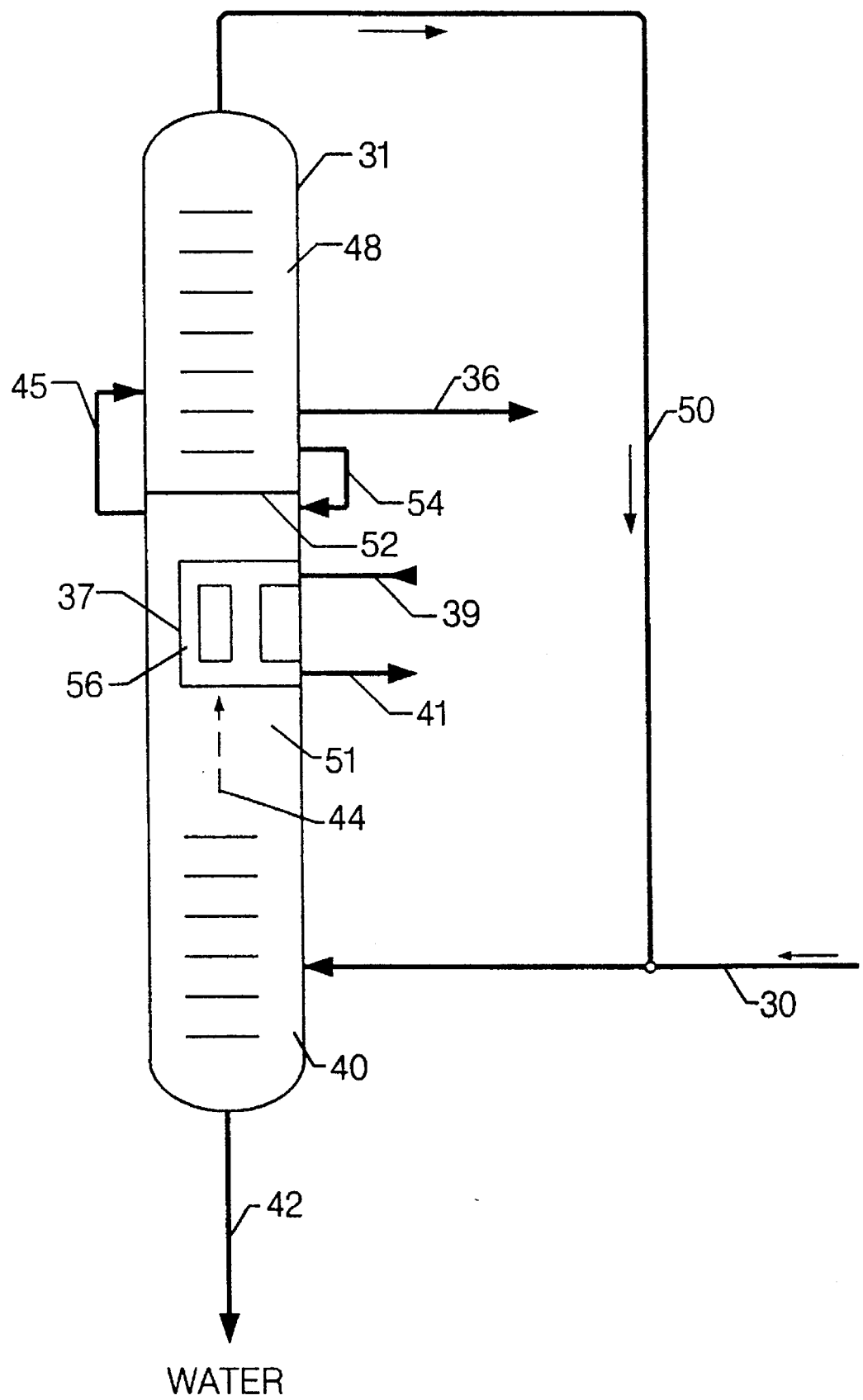

5,614,065

DISTILLATION WITH MEMBRANE APPARATUS

FIELD OF THE INVENTION

The present invention relates to an apparatus to perform distillation by fractionation and membrane separation by vapor permeation in a single vessel. The apparatus is used to separate a process stream containing a first component and a second component into stream containing a substantial amount of the first component and another stream containing a substantial amount of the second component. More specifically, the present invention is an apparatus having a vertically-elongated vessel, a membrane contactor dividing the vessel into an upper portion and lower portion where the membrane contactor is a material providing selective permeation of fluid components and restricting passage of at least one component to the upper portion, a plurality of vertically spaced apart distillation contactors disposed within the vessel for vapor and liquid distillation located in the lower portion of the vessel, means for adding fluid and withdrawing fluid from the lower portion of the vessel, and means for withdrawing fluid from the upper portion of the vessel.

BACKGROUND OF THE INVENTION

In commercial distillation for the separation of one component or a plurality of components from mixtures containing the same, in many instances it is difficult to secure the desired degree of purity. A leading example of the difficulty of separating one component from another component is the breaking of an azeotrope. An azeotropic mixture is defined as a liquid mixture of two or more substances which act as a single substance in that the vapor produced by partial evaporation of the liquid has the same composition as the liquid. The separation of the substances becomes very difficult and expensive.

Azeotropic distillation has been used in the past to circumvent the problems caused when two substances form an azeotropic mixture. In this type of distillation, another substance is added to the azeotropic mixture in order to form another azeotropic mixture with one or more substances of the original mixture. The azeotrope or azeotropes thus formed will have boiling points which differ from the boiling points of the original mixture and will permit greater ease of separation. The problem with azeotropic distillation is that the addition of another substance to a mixture of other substances which need to be separated is not very efficient.

U.S. Pat. No. 4,906,787 (Huang et al.) discloses a process for producing diisopropyl ether containing negligible levels of contaminants, alcohol and water which process comprises hydrating propylene in the presence of an acidic zeolite. The result is an aqueous mixture of ether and alcohol. This aqueous mixture is then passed into a distillation unit operated at conditions which are effective to provide an azeotropic overhead fractionation comprising ether and minor amounts of alcohol and water. The azeotropic overhead fractionation is then passed to an alcohol separation unit which comprises an extraction column that uses process feedwater as the extraction medium. Huang et al. also teaches that the alcohol separation unit can be in the form of a decanter with the condensed azeotropic overheads separating into an ether-rich upper phase and an aqueous alcohol lower phase.

U.S. Pat. No. 4,345,973 (Ladisch et al.) discloses the recovery of ethanol from a fermentation broth comprising the steps of distilling a dilute aqueous alcohol to its azeotrope, distilling the azeotropic mixture using a third component consisting of either an organic solvent or a strong salt solution to break up the azeotrope and remove the remaining water, and distilling the resulting mixture to separate water from this third component.

U.S. Pat. No. 4,774,365 (Chen et al.) discloses a process for producing methyl tertiary butyl ether (MTBE). In the Chen et al. process, excess methanol and isobutylene are fed to an etherification reactor to produce an etherification reactor effluent comprising MTBE, methanol and isobutylene. This excess methanol tends to form azeotropes with the MTBE and isobutylene. To circumvent the azeotrope problem, an etherification effluent stream is passed to a pervaporation membrane to separate the methanol into a methanol-rich permeate vapor stream and an ether-rich raffinate stream. The methanol-rich permeate vapor stream is further cooled and compressed to recover the methanol. The ether-rich raffinate stream is sent to a distillation tower to separate the ether from the isobutylene.

U.S. Pat. No. 5,160,046 (Pasternak) discloses a membrane separation process. In the Pasternak process, an organic oxygen-containing liquid is contacted with a pervaporation membrane consisting of a polyimine polymer layer which has been interfacially crosslinked with a polyisocyanate linking agent to produce a permeate stream of decreased content of an organic oxygen-containing component and a retentate stream of increased content of an organic oxygen-containing component. Pasternak teaches that the process can be employed first and followed by distillation.

There is a need for an apparatus that combines both physical separation processes of distillation by fractionation and membrane separation by vapor permeation in a single vessel to be used in separating a process stream into a first component and a second component.

SUMMARY OF THE INVENTION

The present invention solves the above-identified problem by combining the physical processes of distillation and membrane separation in a single vessel. Such a vessel is used in separating a process stream into a first component and a second component. Combining both distillation and membrane separation in a single vessel reduces capital equipment costs.

The present invention is an apparatus for separating a process stream into at least a first component and a second component within an apparatus having a vertically-elongated vessel, a membrane contactor dividing the vessel into an upper portion and a lower portion where the membrane contactor is a material providing selective permeation of fluid components and restricting passage of at least one component to said upper portion, a plurality of vertically spaced apart distillation contactors disposed within the vessel for vapor and liquid distillation located in the lower portion of the vessel, means for adding fluid and withdrawing fluid from the lower portion of the vessel, and means for withdrawing fluid from the upper portion of the vessel. In a more specific embodiment, the apparatus of the present invention further contains internal passages defined by the material providing selective permeation of fluid components, and means for adding fluids to said internal passages and means for withdrawing fluids from said internal passages In another more specific embodiment, the present invention further contains an additional plurality of vertically spaced apart distillation contactors disposed within the vessel for vapor and liquid distillation located in the upper portion of the vessel. Yet another specific embodiment is one where the apparatus further contains an impermeable flow barrier positioned above the membrane contactor and below the plurality of vertically spaced apart distillation contactors located in the upper portion of the vessel and a conduit external to the vessel to conduct effluent from the membrane contactor to the plurality of vertically spaced apart distillation contactors located in the upper portion of the vessel.

BRIEF DESCRIPTION OF THE DRAWING

The figure is a schematic representation of the preferred apparatus of the present invention.

DESCRIPTION OF THE PREFERRED EMBODIMENT

The present invention combines the physical separations of distillation and membrane separation by vapor permeation in a single vessel. The purpose of the present invention is to provide a means for separating a process stream into a stream comprising a substantial amount of a first component and another stream comprising a substantial amount of a second component. As used herein, "substantial" is defined as greater than about 75 mass %, preferably greater than about 85 mass %, most preferably greater than about 95 mass %.

The apparatus of the present invention is composed of at least two main parts. The first part is a plurality of vertically spaced apart distillation contactors for removing the second component from the process stream by fractionation. The distillation contactors are used to separate the process stream into a distillation overhead stream comprising a substantial portion of the first component and a distillation bottoms stream comprising a substantial amount of the second component. The second part of the invention is a membrane contactor capable of selectively removing the second component from the distillation overhead stream. The membrane contactor separates the distillation overhead stream into a membrane overhead stream comprising a substantial amount of the first component contained in the distillation overhead stream. In a preferred embodiment, the apparatus is a vertically elongated vessel containing a membrane contactor which divides the vessel into an upper portion and a lower portion where both the upper portion and the lower portion contain a plurality of vertically spaced apart distillation contactors. The apparatus also contains means for introducing and withdrawing fluid from the lower portion of the vessel, and means for withdrawing fluid from the upper portion of the vessel.

The process stream to be separated can be any fluid stream which contains a first component and a second component. For example, the stream could be a mixture of an alcohol such as ethanol, isopropyl alcohol, n-propyl alcohol, sec-butyl alcohol, or cyclohexanol, and water. Each component may be a single constituent or a plurality of constituents.

The distillation contactors may be such internals as trays or packings to provide at least two theoretical stages of contact to assist in removing the second component by fractionation from the process stream. The trays or packings may be of conventional nature. Such trays or packings are very well known to those skilled in the art and do not require extensive discussion here. In one embodiment of the present invention, the apparatus of the present invention is a vessel having two sets of distillation contactors, one set in the portion of the vessel above the membrane contactor and one set in the portion of the vessel below the membrane contactor. Each of the distillation contactors can be converted into reactive distillation contactors by disposing catalyst therein. The reactive distillation contactors serve both to remove the second component and to react the first component to form a more desirable third component.

The membrane contactor divides the vessel into two portions by at least partially occluding the flow path or the cross section of the vessel and provides selective permeation of fluid components and restricting the passage of at least one component to the upper portion of the vessel. The membrane contactor is preferably a hollow tube type membrane where the membrane defines internal passages which have means for adding fluids to said internal passages and means for withdrawing fluids from said internal passages, and the membrane is capable of separating at least one first component from a second component by vapor permeation. For example, at least one of the components contained in the distillation overhead stream would have a very low rate of permeation through the membrane and into the internal passage and therefore would remain in the vessel to be contained in the membrane overhead stream. Or, in other words, only select components would have a high rate of permeation through the membrane and into the internal passage of the membrane to be conducted from the vessel through the internal passage via a carrier fluid and therefore be removed from the membrane overhead stream. By maintaining a partial pressure differential across the membrane, which is usually a pressure drop from about 1 to about 50 psia, the first component preferentially permeates the membrane, thereby moving from the exterior of the membrane into the internal passage of the membrane. The interior side of the membrane can be equipped with a pressure decreasing means which is usually a carrier fluid in order to decrease the pressure on the interior side and achieve better diffusion of the permeate through the membrane. The carrier fluid also serves to sweep the components through the internal passages of the membrane and remove them from the vessel. The carrier fluid may be compounds such as nitrogen, hydrogen, helium, or low carbon number hydrocarbons such as propane and butane. Typically the carrier fluid is heated prior to being introduced into the internal passage to prevent components from condensing in the internal passage.

The membrane contactor may consist of one or more units or bundles which in turn may consist of a single membrane device or, alternatively, several membrane devices integrated and operated so as to achieve the separation in the most efficient manner, for example, a cascade of membrane units with an internal recycle stream between various stages of the membrane unit. In one embodiment of the present invention, the membrane contactor consists of modules, each having certain membrane areas for permeation and also appropriate heat exchangers to compensate for the cooling effect due to permeation. The membrane contactor may transverse at least partially across the vessel at an angle or horizontally. The operating pressure of the membrane unit can range from about 1 to about 150 atmospheres, or higher, and the temperature can range from about 35° F. to about 300° F.

In the specific embodiment where the fluid components to be separated are an alcohol and water, the membrane used in the membrane contactor can be any composite suitable for use in separating alcohols from water by vapor permeation including, but are not limited to, a nonporous polyimine, preferably a polyimine which has been interfacially crosslinked with a polyisocyanate or with a poly(carbonyl) chloride, a polyacrylonitrile polymer, a polysulfone polymer, a film of perfluorosulfonic acid polymer on a porous matrix polytetrafluoroethylene, a polyvinyl alcohol and a polyacrylic acid on a polyacrylonitrile support layer. Suitable physical characteristics for the membrane include a thickness of about 5 to about 80 microns and a molecular weight limit of about 40,000 to about 50,000.

The preferred membrane contactor is a polyimide membrane with an asymmetric structure. Such a membrane should have excellent chemical tolerance and high thermal stability and selectivity. The polyimide membrane is produced by the condensation polymerization of biphenyltetracarboxylic dianhydride and aromatic diamines. Its chemical structure is:

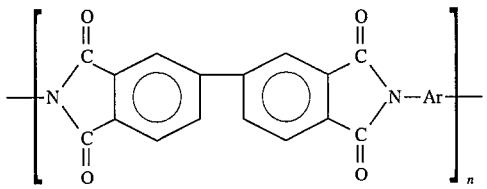

The polyimide membrane is a type of hollow fiber with an asymmetric structure having a dense layer on a microporous support. The dense layer serves to separate a gas mixture and is designed to be ultrathin in order to obtain a practical permeation rate. The microporous support of the membrane reinforces the dense layer and has a minimum effect on the gas separation. The hollow fiber is uniformly made in a one-step process from the polyimide dope and is wholly made of the same material.

In one embodiment of the present invention, the membrane contactor is a membrane assembly including a carrier layer which provides mechanical strength, a porous support layer, and a separating layer across which separation occurs. The carrier layer is typically characterized by a high degree of porosity and mechanical strength and may be fibrous or nonfibrous, woven or nonwoven. The porous support layer can be a polyacrylonitrile or polysulfone polymer. The separating layer can be a nonporous film or membrane, e.g., a polyimide polymer crosslinked by urea or amide linkages.

The apparatus of the present invention is useful in many processes, particularly in the hydrocarbon processing area. The use of the invention is best explained in terms of the specific application where the stream to be separated is a mixture of isopropyl alcohol and water with the first component being isopropyl alcohol and the second component being water, and the apparatus of the invention is a vessel containing a membrane contactor dividing the vessel into an upper portion and a lower portion where the lower portion contains a plurality of vertically spaced apart distillation contactors. Typically, the isopropyl alcohol and water mixture will be the effluent from an isopropyl alcohol production process, and the water will be present in an excess amount. Commonly expected concentrations are, for example, 82 mass % water and 18 mass % isopropyl alcohol. The present invention, being only a single vessel, significantly reduces both capital costs and operational costs of the separation incurred in separating isopropyl alcohol and water as compared with the two-unit systems, usually an azeotrope column and a distillation column, currently used in industry.

The stream containing the isopropyl alcohol and water mixture is introduced into the lower portion of the vessel where a majority of the water is easily separated by fractionation using the distillation contactors and removed from the isopropyl alcohol in a distillation bottoms stream due to the difference in boiling points of the water and the alcohol. As the concentration of water in the mixture decreases, an azeotrope of 88 mass % isopropyl alcohol and 12 mass % water will form and additional water will not be separated from the azeotrope in the lower portion through distillation. The distillation overhead stream then encounters the membrane contactor which is, e.g., a polyimide hollow fiber membrane capable of selectively removing water from the distillation overhead stream. A portion of the water present in the distillation overhead stream permeates the membrane contactor and enters into the internal passage of the polyimide hollow fiber membrane and is conducted through the internal passage and out of the apparatus using a heated carrier fluid thereby causing the concentration of water in the membrane overhead to fall below that required to maintain the azeotrope. Or, in other words, the isopropyl alcohol, which has a comparatively low rate of permeation into the internal passage of the hollow fiber membrane, is retained in the apparatus and forms the main component for the membrane overhead stream. In this embodiment of the invention, the membrane contactor and operating conditions are chosen so that sufficient water is removed to result in a membrane overhead stream containing at least 98 mass % isopropyl alcohol which is then removed from the vessel and collected.

Removing sufficient water to provide a stream of at least 98 mass % isopropyl alcohol may be difficult, so another embodiment of the invention is one where only a portion of the water available is removed by the membrane contactor, and a second set of distillation contactors are employed in the upper portion of the vessel to separate any alcohol and water azeotrope from the alcohol. For this embodiment, the apparatus of the invention is a vessel containing a membrane contactor dividing the vessel into an upper portion and a lower portion where both the upper portion and the lower portion contain a plurality of vertically spaced apart distillation contactors, means for adding fluid and withdrawing fluid from the lower portion of the vessel, and means for withdrawing fluid from the upper portion of the vessel. In general terms, using this embodiment involves (1) introducing a process stream to the lower portion of the vessel and distilling the process stream, using the distillation contactors, into a lower distillation overhead stream enriched in a first component and a lower distillation bottoms stream enriched in a second component; (2) conducting the lower distillation overhead stream to the membrane contactor and selectively removing a portion of the second component from the lower distillation overhead stream to afford a membrane overhead stream which is depleted in the second component; (3) passing the membrane overhead stream to the upper portion of the vessel and distilling using the distillation contactors to form an upper distillation bottoms stream containing at least 98 mass % first component and an upper distillation overhead stream; and (4) withdrawing and collecting the upper distillation bottoms stream from the upper portion of the vessel.

As applied to the specific embodiment where the stream to be separated is a mixture of isopropyl alcohol and water with the first component being the alcohol and the second component being the water, the use of the invention would proceed as follows. The stream containing the isopropyl alcohol and water mixture is introduced into the lower portion of the vessel where a majority of the water is easily separated and removed from the isopropyl alcohol in a lower distillation bottoms stream due to the difference in boiling points of the water and the alcohol. As the concentration of water in the mixture decreases, an azeotrope of 88 mass % isopropyl alcohol and 12 mass % water will form, and additional water will not be separated from the azeotrope in the distillation. The lower distillation overhead stream then encounters the membrane contactor where the water selectively permeates through the membrane and is removed causing the concentration of water in the membrane overhead stream to fall below that required to maintain the azeotrope. The membrane contactor and operating conditions are chosen so that only a portion of the available water is removed resulting in a membrane overhead stream requiring further distillation. The membrane overhead stream is then introduced to the upper portion of the vessel where isopropyl alcohol may be separated from the isopropyl alcohol and water azeotrope that reforms with the removal of isopropyl alcohol due to the slight, yet sufficient, difference in the boiling points of the alcohol and the azeotrope. An upper distillation bottoms stream of at least 98 mass % isopropyl alcohol may be removed from the vessel and collected, and the upper distillation overhead stream containing the azeotrope may be recycled to the lower portion of the vessel.

Applicant has found that with the embodiment having distillation contactors in both the lower and upper portions of the vessel, it is preferred that the vessel also have an impermeable barrier between the membrane contactor and the first distillation contactor of the upper portion of the vessel. The membrane overhead stream is directed in a line external or internal to the vessel and is introduced to the upper portion of the vessel at least a short distance from the first distillation contactor of the upper portion. For example, when the distillation contactors are comprised of a series of trays, the membrane overhead stream should be introduced at least two trays into the upper portion. The stream containing substantially the first component is withdrawn from the upper portion of the vessel in the segment of the upper portion after the beginning of the upper portion and before the introduction of the membrane overhead stream. Since the membrane overhead stream is introduced at a point after the withdrawal of the first component stream, there is less opportunity for mixing, and the concentration of the first component in the first component stream is higher. Of course, a conduit allowing for non-removed liquid to pass to the membrane contactor may be provided.

The apparatus of the present invention may also be incorporated into a two-stage diisopropyl ether producing process to assist in breaking the isopropyl alcohol-water azeotrope that is formed during the production of diisopropyl ether. In the first stage of the two-stage diisopropyl ether process, a propylene-containing stream is passed to a first stage diisopropyl ether formation reactor and reacted with recycled isopropyl alcohol to form diisopropyl ether in the presence of an etherification catalyst.

The propylene-containing stream can include, but is not limited to, gas plant off-gas containing propylene, naphtha cracker off-gas containing light olefins, and refinery fluidized catalytic cracked (FCC) propane/propylene streams. The concentration of propylene used will vary depending upon the source of the propylene. These sources provide a propylene/propane mixture comprising about 60 to about 80 vol. % propylene. In a preferred embodiment, the propylene concentration of the propylene-containing stream is less than about 70 vol. %.

The etherification catalyst can be any catalyst suitable for propylene conversion. Suitable etherification catalysts include zeolites and ion exchange resins. With respect to zeolites, both intermediate and large pore zeolites can be used. Of particular interest for use herein are large pore acidic zeolites, e.g. zeolite Beta, X, L, Y, ultra stable Y, rare earth Y, ZSM-3, ZSM-4, ZSM-12, ZSM-20, and ZSM-50. With respect to the ion exchange resin, a synthetic ion exchange resin is preferred. The preferred ion exchange resin has three components: (1) the raw material which is used for the construction of the skeleton or matrix; (2) bridging agents for cross-linking and insolubilization; and (3) the type and number of functional active groups. With respect to forming the ion exchange resin matrix, polymerization and polycondensation can be used as the synthesis route. polymerization is preferred because the matrices resulting therefrom generally have higher chemical and thermal stability. The preferred starting material for synthesizing the catalyst of the present invention is styrene. The styrene is polymerized with itself and with divinylbenzene into a polymeric molecule:

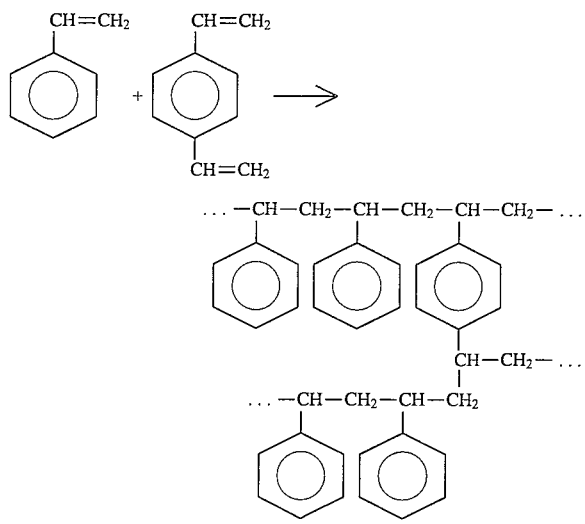

Matrices for the catalyst of the present invention can also be prepared using: (1) a divinylbenzene and an acrylic acid or methacrylic acid or;

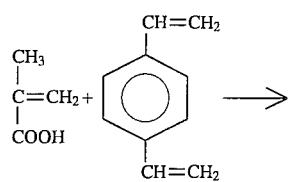

-continued

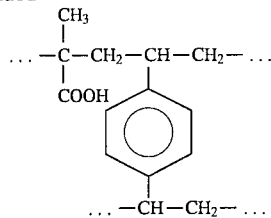

(2) phenol and formaldehyde;

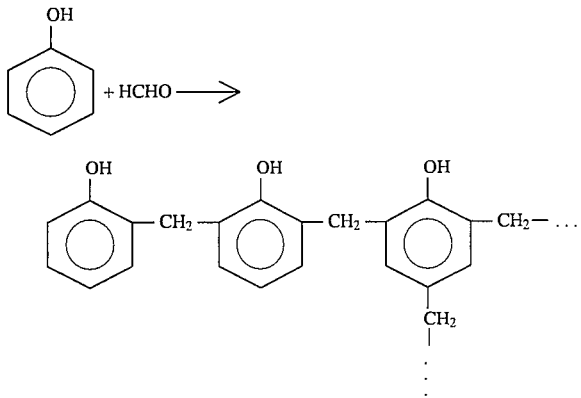

In the case of divinylbenzene-containing matrices, crosslinking depends on the quantity of divinylbenzene used as the crosslinking agent. The nature and degree of crosslinking can have a profound effect on the ion exchange properties of the catalyst. The amount of divinylbenzene used can range from about 2 to about 12 wt. %. With respect to the structure of the network of synthetic ion exchange resins, different types are now available with designations such as gel and macroporous ion exchange resins. With respect to gel-type ion exchange resins during the polymerization of styrene and divinylbenzene, the network formed is obtained as a gel. The properties of such a co-polymer can be varied by changing the ratios of the amounts of the individual monomers used during the synthesis. These gel-type polymer structures have no appreciable porosity until they are swollen in suitable medium; but such crosslinked polymers swell to a well-defined and reproducible degree in an appropriate solvent system such as toluene. Macroporous ion exchange resins are types in which a solvent is used during production from the monomers so that a porous matrix structure is formed in the course of polymerization. The ion exchange resins may be crosslinked and the pore size modified in a way to obtain polymers with a substantially uniform pore size.

It is preferred that the first stage diisopropyl ether formation catalyst is a cation exchange resin comprising $SO_3H$ groups. Suitable cation exchange resins include, for example, sulfonated organic resins in their acidic form. Of particular importance are sulfonated polystyrene resins such as the $SO_3H$ groups containing co-polymers of aromatic monovinyl compounds and aromatic polyvinyl compounds. Especially preferred cation exchange resins are sulfonated styrene/divinylbenzene co-polymers, for example, "Amberlyst 36." These cation exchange resins are produced by the sulfonation of suspension co-polymer beads with sulfuric acid, sulfur trioxide, fuming sulfuric acid or chlorosulfonic acid. The $SO_3$ groups which are the ionic groups yielding the cation exchange function can be in the para position.

The etherification catalyst can have a surface area of about 1 to about 100 $m^2/g$, preferably approximately 35 and a porosity of about 0.05 to about 0.5 ml/g, preferably about 0.30 ml/g.

Suitable conditions for the first stage diisopropyl ether formation reactor include a temperature of about 200° to about 300° F., a pressure of about 100 to about 1200 psig, preferably about 700 to about 1000 psig, and an isopropyl alcohol to propylene ratio of about 0.1:1 to about 2:1, preferably about 0.6:1.

In the first stage reactor, etherification can be carried out under liquid phase, vapor phase or mixed vapor-liquid phase conditions in a batch or continuous manner. With respect to the first stage diisopropyl ether formation reactor, a stirred tank reactor or fixed bed reactor can be employed. The flow of reactants and products can be liquid-upflow, liquid-downflow, countercurrent, or cocurrent, a liquid hourly space velocity of about 0.1 to about 20, preferably about 0.1 to about 2 when operating in the continuous mode. In a preferred embodiment, the single stage reactor can be a liquid phase fixed-bed reactor with recirculation of cooled etherification means effluent for temperature control.

An effluent containing diisopropyl ether, isopropyl alcohol, propylene and propane from the first stage diisopropyl ether formation reactor is passed to a light ends recovery unit where propylene and propane are removed. Effluent from the light ends recovery unit is passed to a water wash tower where isopropyl alcohol is removed to produce an extract comprising residual isopropyl alcohol and water and a raffinate stream comprising a diisopropyl product stream.

Regardless of whether the first stage effluent stream is treated to remove light ends or residual isopropyl alcohol, at least a portion of the diisopropyl ether product stream is passed to a second stage isopropyl alcohol formation reactor where diisopropyl ether is reacted with water in the presence of a hydration catalyst under conditions sufficient to produce a second stage effluent stream comprising isopropyl alcohol, water and a small amount of diisopropyl ether.

The hydration catalyst suitable for use in the isopropyl alcohol formation reactor is the same as the etherification catalyst described above, although a catalyst which is more suitable for reaction with high levels of water and at increased temperatures is preferred. Suitable conditions for the isopropyl alcohol formation reactor include a temperature of about 250° to about 350° F., a pressure of about 100 to about 500 psig, preferably about 300 to about 400 psig, and a water to diisopropyl ether ratio of about 1:1 to about 50:1, preferably about 10:1.

In the isopropyl alcohol formation reactor, hydration of diisopropyl ether can be carried out under liquid phase, vapor phase or mixed vapor-liquid phase conditions in a batch or continuous manner. Further, with respect to the isopropyl alcohol formation reactor, a stirred tank reactor or fixed bed reactor can be employed. The flow of reactants and products can be trickle-bed, liquid-upflow, liquid-downflow, countercurrent, or cocurrent having a liquid hourly space velocity of about 0.05 to about 20, preferably about 0.1 to about 2 when operating in the continuous mode.

The effluent stream from the isopropyl alcohol formation reactor and the extract from the water wash column are both passed to the apparatus of the present invention to separate alcohol from water. The apparatus of the present invention consists of a vertically-elongated vessel containing a membrane contactor dividing the vessel into an upper portion and lower portion where the membrane contactor is a material providing selective permeation of fluid components, a plurality of vertically spaced apart distillation contactors disposed within the vessel for vapor and liquid distillation located in the lower portion of the vessel, a second plurality of vertically spaced apart distillation contactors disposed within the vessel for vapor and liquid distillation located in the upper portion of the vessel, means for adding fluid and withdrawing fluid from the lower portion of the vessel, and means for withdrawing fluid from the upper portion of the vessel. Accordingly, a mixture of water and isopropyl alcohol is introduced to the lower portion of the vessel where the mixture is separated by distillation using the distillation contactors into a lower distillation overhead stream having an alcohol concentration of at least about 80 mass % and a lower distillation bottoms stream having a water concentration of at least about 90 mass %.

The lower distillation overhead stream encounters the membrane contactor which contains a hollow tube type membrane capable of allowing selective permeation and removal of water. The water, with its high rate of permeability, enters into the internal passage within the hollow tube membrane. Once in the internal passage, the water is conducted through the internal passage and out of the apparatus using a heated carrier fluid. A membrane overhead stream, of reduced water content, exits the membrane contactor and enters the upper portion of the vessel. In the upper portion of the vessel, the membrane overhead stream is separated by distillation using the distillation contactors, into an upper distillation overhead stream having an isopropyl alcohol and water azeotrope and an upper distillation bottoms stream having an isopropyl alcohol concentration of at least about 98 mass %. The upper distillation overhead stream is recycled to the lower portion of the vessel and the upper distillation bottoms stream containing a substantial amount of the isopropyl alcohol is removed from the upper portion of the vessel and recycled to the diisopropyl ether formation reactor.

The figure is a schematic representation of one embodiment of the apparatus of the present invention. The apparatus consists of vertically-elongated vessel 31 containing three major operating parts: (1) lower portion 40; (2) membrane contactor 51 positioned above lower portion 40 and in fluid communication with lower portion 40; (3) and upper portion 48 positioned above the membrane contactor 51 and in fluid communication with membrane contactor 51. Membrane contactor 51 has hollow fiber type polyimide membrane 37. Stream 39 introduces heated nitrogen carrier fluid into the internal passage 56 of the hollow fiber membrane 37. Water has a high rate of permeability into the internal passage 56 of the membrane 37 and is conducted through the internal passage 56 and removed in stream 41. The isopropyl alcohol has a comparatively low rate of permeability into the internal passage 56.

Further referring to the figure, an effluent from a diisopropyl ether plant (not shown) containing a mixture of 50 mass % isopropyl alcohol and 50 mass % water is introduced to lower portion 40 via line 50. Exiting the bottom of lower portion 40 is lower distillation bottoms stream 42 having a water concentration of about 90 mass %. Exiting the top of lower portion 40 is a lower distillation overhead stream which is shown by internal stream dotted line 44. Stream 44 is an azeotropic mixture of isopropyl alcohol and water having a composition of 88 mass % alcohol and 12 mass % water.

A membrane overhead stream 45 having an alcohol concentration of about 94 mass % exits above membrane contactor 51, is conducted around physical barrier 52 and enters upper portion 48. In upper portion 48, a water and isopropyl alcohol azeotrope continues to be removed from membrane overhead stream 45. Exiting the top of upper portion 48 is an upper distillation overhead stream 50. Upper distillation overhead stream 50 is recycled to lower portion 40. Exiting the bottom of upper portion 48 is an upper distillation bottoms stream 36 which has an alcohol concentration of at least 98 mass %. Note that the point at which the upper distillation bottoms stream 36 is removed is between the beginning of upper portion 48 and the introduction of the membrane separation overhead stream 45.

What is claimed is:

1. An apparatus for separating fluid components comprising:
   a. a vertically-elongated vessel;
   b. a membrane contactor at least partially occluding the flow path through said vessel and dividing the vessel into an upper portion and lower portion, said membrane contactor comprising material providing selective permeation of fluid components and restricting passage of at least one component to said upper portion;
   c. a plurality of vertically spaced apart distillation contactors disposed within said lower portion of said vessel for vapor and liquid distillation; and
   d. means for adding fluid and withdrawing fluid from the lower portion of the vessel, and means for withdrawing fluid from the upper portion of the vessel.

2. The apparatus of claim 1 further comprising a plurality of vertically spaced apart distillation contactors disposed within said upper portion of said vessel for vapor and liquid distillation.

3. The apparatus of claim 2 further comprising an impermeable flow barrier positioned above the membrane contactor and below the plurality of vertically spaced apart distillation contactors located in said upper portion of the vessel, and a conduit to communicate effluent from above the membrane contactor past said impermeable flow barrier to the plurality of vertically spaced apart distillation contactors located in said upper portion of the vessel.

4. The apparatus of claim 1 where said distillation contactors contain a catalyst for reactive distillation.

5. The apparatus of claim 1 further comprising internal passages defined by said material providing selective permeation of fluid components, and means for adding fluid and withdrawing fluid from said internal passages.

6. The apparatus of claim 1 where said material comprises a nonporous polyimine.

7. The apparatus of claim 6 where said nonporous polyimine is interfacially crosslinked with a polyisocyanate.

8. The apparatus of claim 1 where said material comprises a hollow fiber membrane.

9. The apparatus of claim 1 where said material comprises perfluorosulfonic acid polymer on a porous matrix polytetrafluoroethylene.

10. The apparatus of claim 1 where said material comprises a polyacrylic add on a polyacrylonitrile support layer.

11. An apparatus for separating fluid components comprising:
    a. a vertically-elongated vessel;
    b. a membrane contactor at least partially occluding the flow path through said vessel and dividing the vessel into an upper portion and lower portion, said membrane contactor comprising material providing selective permeation of fluid components and defining internal passages;
    c. means for adding fluid and withdrawing fluid from said internal passages;
    d. a plurality of vertically spaced apart distillation contactors disposed within said lower portion of said vessel for vapor and liquid distillation; and c. means for adding fluid and withdrawing fluid from the lower portion of the vessel, and means for withdrawing fluid from the upper portion of the vessel.

12. The apparatus of claim 11 further comprising a plurality of vertically spaced apart distillation contactors disposed within said upper portion of said vessel for vapor and liquid distillation.

13. The apparatus of claim 12 further comprising an impermeable flow barrier positioned above the membrane contactor and below the plurality of vertically spaced apart distillation contactors located in said upper portion of the vessel, and a conduit to communicate effluent from above the membrane contactor past said impermeable flow barrier to the plurality of vertically spaced apart distillation contactors located in said upper portion of the vessel.

14. The apparatus of claim 11 where said distillation contactors contain a catalyst for reactive distillation.

15. The apparatus of claim 11 where said material comprises a nonporous polyimine.

16. The apparatus of claim 15 where said nonporous polyimine is interfacially crosslinked with a polyisocyanate.

17. The apparatus of claim 11 where said material comprises a hollow fiber membrane.

18. The apparatus of claim 11 where said material comprises perfluorosulfonic acid polymer on a porous matrix polytetrafluoroethylene.

19. The apparatus of claim 11 where said material comprises a polyacrylic acid on a polyacrylonitrile support layer.

\* \* \* \* \*